United States Patent [19]

Hempel

[11] Patent Number: 5,507,776
[45] Date of Patent: Apr. 16, 1996

[54] SURGICAL STAPLE SUTURING MEANS

[75] Inventor: Sven Hempel, Kaltenkirchen, Germany

[73] Assignee: Ethicon Endo-Surgery, Inc., Cincinnati, Ohio

[21] Appl. No.: 245,733

[22] Filed: May 18, 1994

[30]   Foreign Application Priority Data

Jun. 4, 1993 [DE] Germany ............................ 43 19 105.3

[51] Int. Cl.$^6$ .................................................. A61B 17/04
[52] U.S. Cl. ........................... 606/219; 24/457; 24/711.1; 606/220
[58] Field of Search ........................... 24/93, 97, 102 PL, 24/711.1, 457; 606/219–220

[56]         References Cited

U.S. PATENT DOCUMENTS

| 1,184,590 | 5/1916 | Stewart | 24/711.1 |
| 2,586,434 | 2/1952 | Marien | 24/102 PL |
| 2,859,501 | 11/1958 | Pero | 24/97 |

FOREIGN PATENT DOCUMENTS

| 2639413 | 7/1977 | Germany | A61B 17/08 |
| 3022087 | 1/1981 | Germany | A61B 17/12 |

*Primary Examiner*—Gary Jackson
*Attorney, Agent, or Firm*—Paul A. Coletti

[57]            ABSTRACT

A surgical staple means for the induction of wound sutures which consists of a base and a top layer connected to the suture base via stems, the tissue layers being pressed together between the base and the top layer, is designed in one part. The strip-shaped base comprises a plurality of prong-shaped staple elements which are arranged perpendicular to the plane of the base at a defined distance one behind the other in a row or in several parallel rows. Each staple element comprises a stem which is rigid relative to the base and a piercer pivotally connected to the stem, the piercers being equidirectionally foldable for the formation of the top layer of the staple means after the penetration of the tissue layers, the piercers also comprising locking elements which provide a form-locking connection of neighboring piercers. A device for the induction of the staple means is also described.

3 Claims, 7 Drawing Sheets

5,507,776

SURGICAL STAPLE SUTURING MEANS

PRIORITY APPLICATION

This application claims priority from DE 43 19 105.3, filed Jun. 4, 1993.

BACKGROUND OF THE INVENTION

This invention relates to a surgical staple means for the inducement of the raid and gentle adaption of wound closure. In particular, the invention relates to a staple means with which the tissue layers in question are joined in a suture-like fashion.

Known according to the prior art are conventional technologies in which the tissue margins are artificially brought together (according to the type of tissue or organ) by means of a steel needle guiding a thread in order to achieve firm fixing until healing.

Besides this conventional technology, clipping with metal staples represents a particular way of bringing wound margins together. Thus, a staple technique is known which is based on the principle of "suturing" by means of wire staples. A row of wire staples made from metal is inserted into a special stapler apparatus and positioned at the wound to be joined. The tips of the wire staples are pushed through the tissue by means of a wedge-shaped feed device and shaped by suitable anvil pockets in such a way that the staple legs sink themselves into the tissue. This allows the tissue layers to be joined after the removal of the stapler apparatus from the wound site.

The disadvantage of this stapling technique is that only wire staples made from metal follow the necessary permanent deformation at their free ends, thus guaranteeing the fixation involved.

Also known in the art is a surgical securing system made from resorbable material with which tissue margins of organs or skin are connected for the purpose of healing. This system consists of a strip-shaped base made from a number of interconnected receiving elements, each of the receiving elements having a pair of similar openings. The base is placed in position at the tissue margins and, from the opposite side of the tissue layer, the limbs of U-shaped staples which are pointed at the ends are pressed through the tissue layer into the openings of the base. Because both the openings and the limbs of the staples re designed with corresponding locking elements, an inseparable connection of the securing system results.

The disadvantage of this solution is that the securing system is formed from several individual fastener parts which have to be positioned relative to one another when producing the sound suture, and can be loaded as a magazine only in a very time-consuming manner. This is realized only at great cost by means of suitable staple-inducing devices. Another disadvantage is that an extremely large amount of resorbable material is introduced into the body.

SUMMARY OF INVENTION

The object of the invention is to provide a staple means which facilitates the inducement of wound healing while using resorbable material. This is achieved according to the invention by designing the staple means in exclusively one piece; the strip-shaped suture base comprises a plurality of prong-shaped staple elements which are arranged perpendicular to the plane of the suture base at a defined distance, one behind the other in a row or in several parallel rows. Every staple element consists of a stem which is rigid relative to the suture base and a piercer pivotally connected to the stem; the piercers being equidirectionally foldable for the formation of the top layer of the staple means after the penetration of the tissue layers; and further comprising Docking elements which provide a form-locking connection of neighboring piercers.

Compared with a staple means designed in several parts, the design in one part achieves, for the same mechanical properties, a reduction in the resorbable material introduced into the body.

According to another feature of the invention, an apparatus for inducing the wound suture is provided. This apparatus is formed from a proximal actuation mechanism, a distal staple applying device, and a rod system lying between them. The distal staple-induction device consists of two clamping jaws, of which the lower clamping jaw is rigid relative to the device and the upper clamping jaw can be opened around a hinge by means of a push rod, in the manner of forceps. The lower clamping jaw is provided with a support surface, displaceable transversely relative to the tissue layer, which is fitted with means for fixing the base of the staple means in such a way that the staple elements are directed with their tips towards the upper clamping jaw. Arranged in the upper clamping jaw is a comb-shaped counter-bearing surface or anvil which projects between the staple elements and has means permitting a displacement of the anvil bearing in a distal direction, which effects the simultaneous and equidirectional folding over of the piercers and their form-locking reciprocal retention.

Another feature of the invention relates to an individual staple for use according to the invention. The staple is formed from a base and a top layer connected to the base via stems, the tissue layers being pressed together between the suture and the top layer. It consists of a section forming the base, at which are arranged two stems penetrating the tissue layers; and at least one of the stems which emerge from the tissue layers comprising a bending zone, which allows a folding over of this stem in the direction of the other stem. Both stems are provided at their free ends with means for form-locking reciprocal retention, for the formation of a top layer parallel to the base.

DESCRIPTION OF THE DRAWINGS

The invention will be described in more detail with reference to an embodiment. The associated drawings show in FIG. 1 is a perspective view of a staple means of a first version prior to use.

DETAILED DESCRIPTION INVENTION

Figure 1:
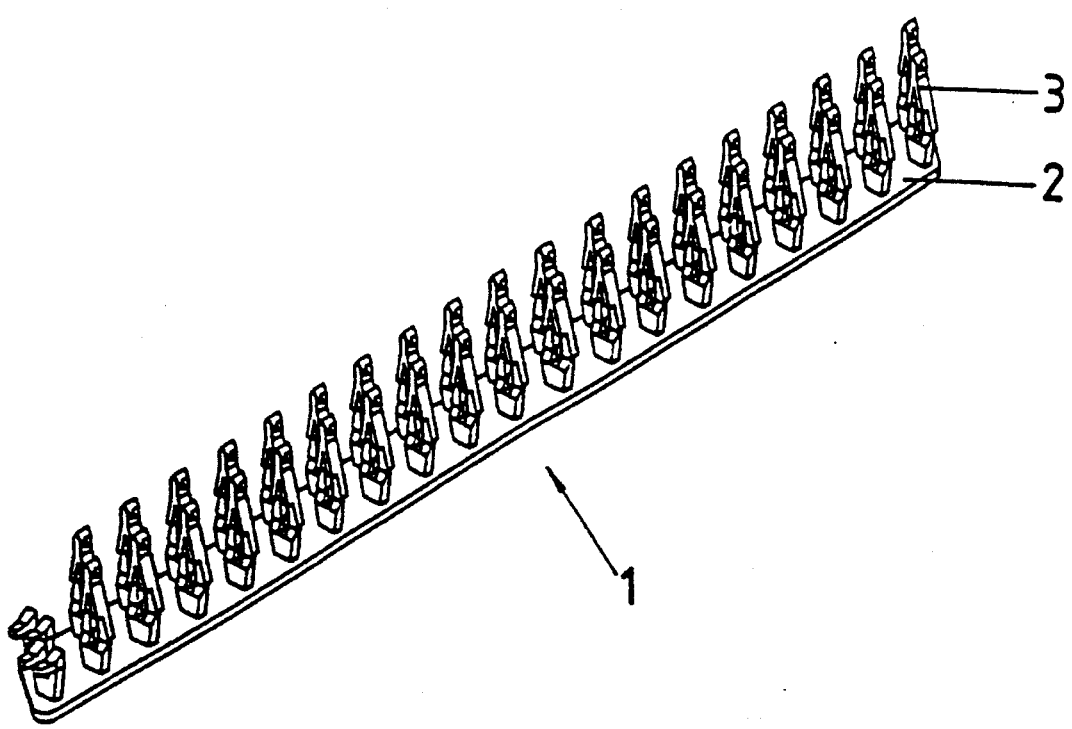
Figure 2:
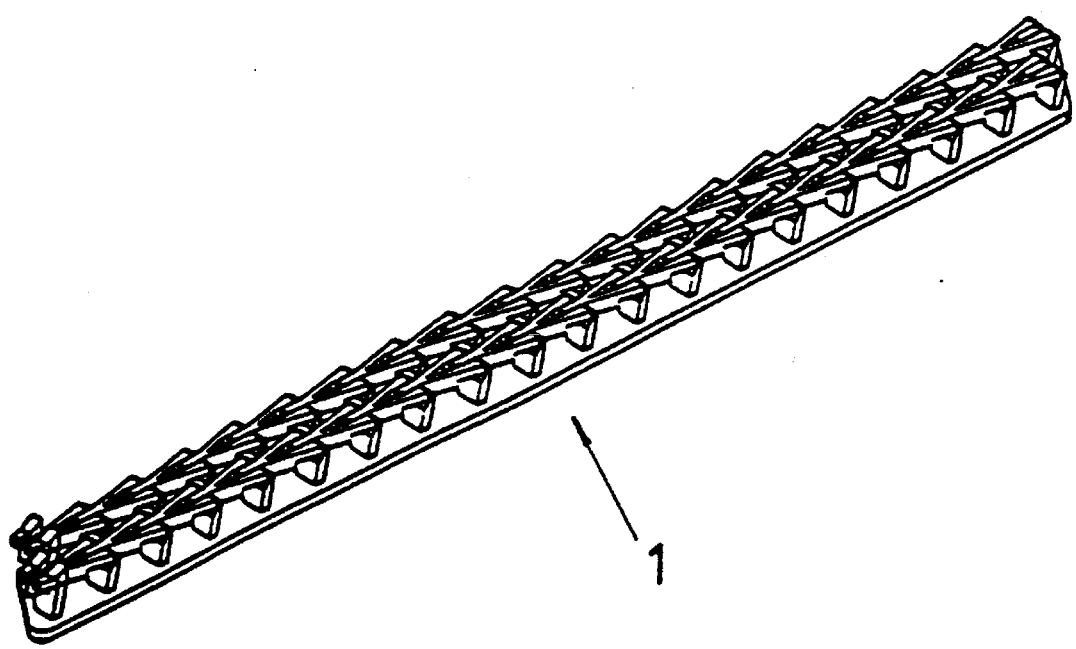
FIG. 2 is a perspective view of the staple means according to FIG. 1 in action according to the invention.
Figure 3:
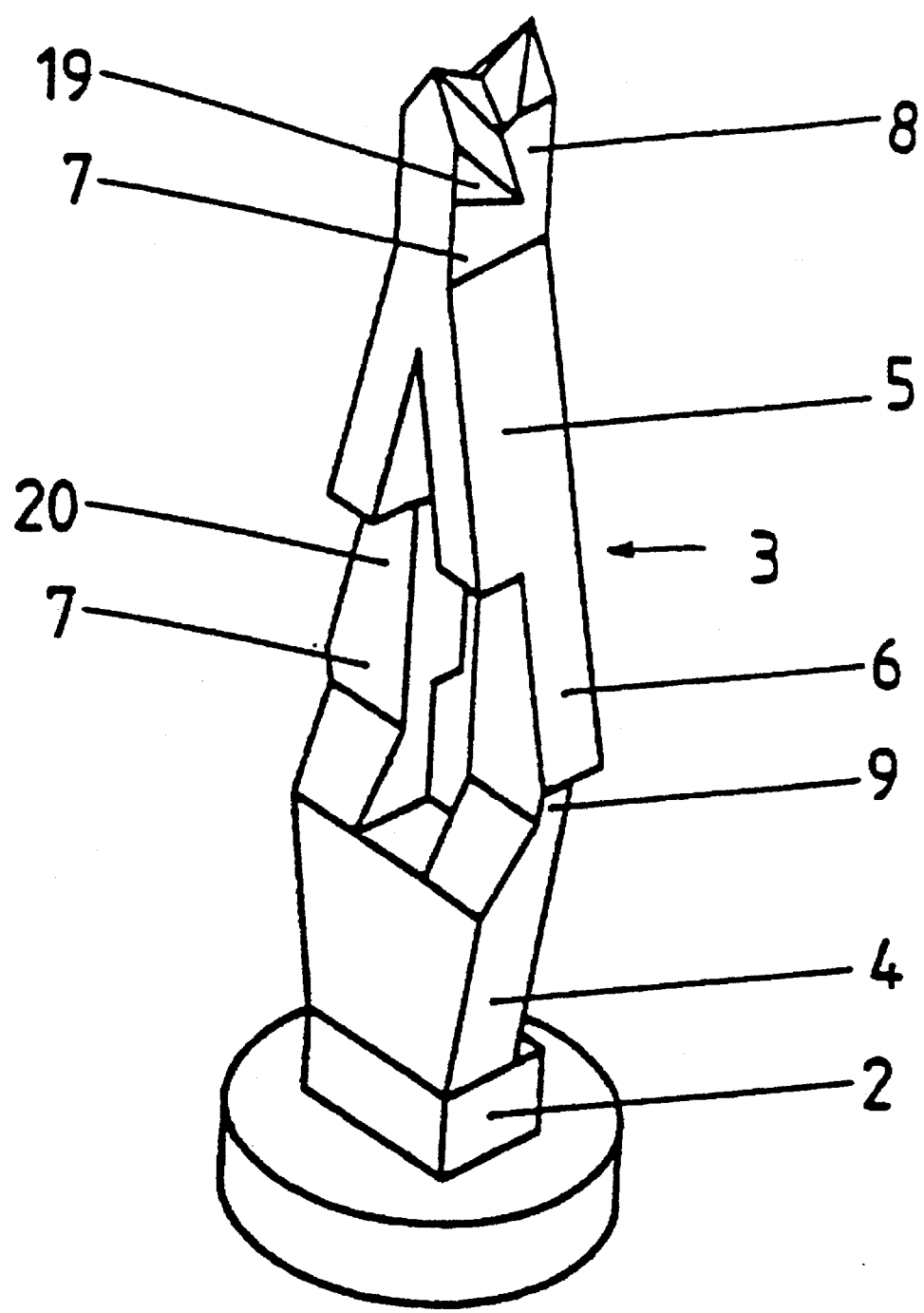
FIG. 3 is a perspective view of a staple element according to FIG. 1.
Figure 4:
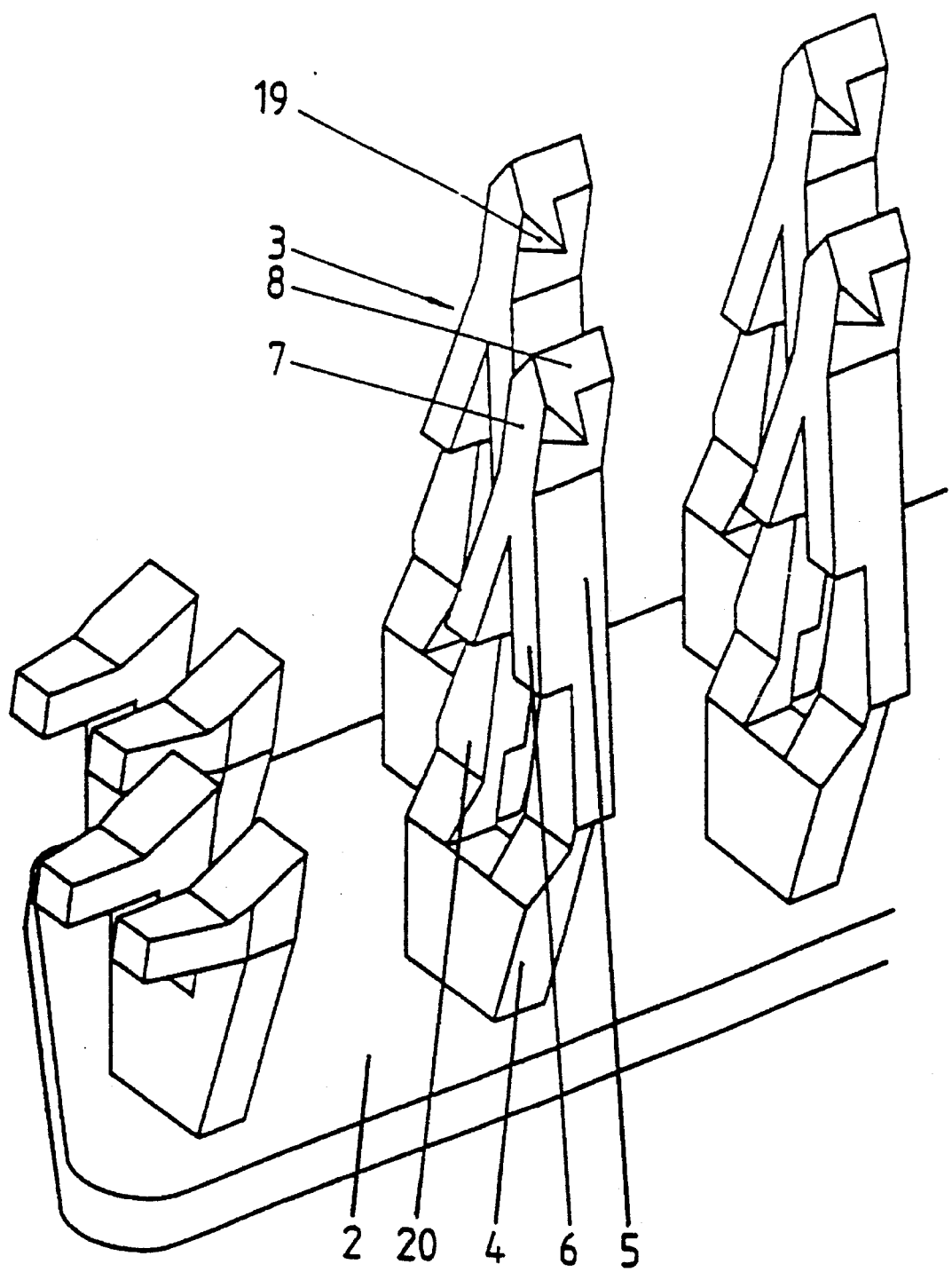
FIG. 4 is an enlarged section from FIG. 1.
Figure 5:
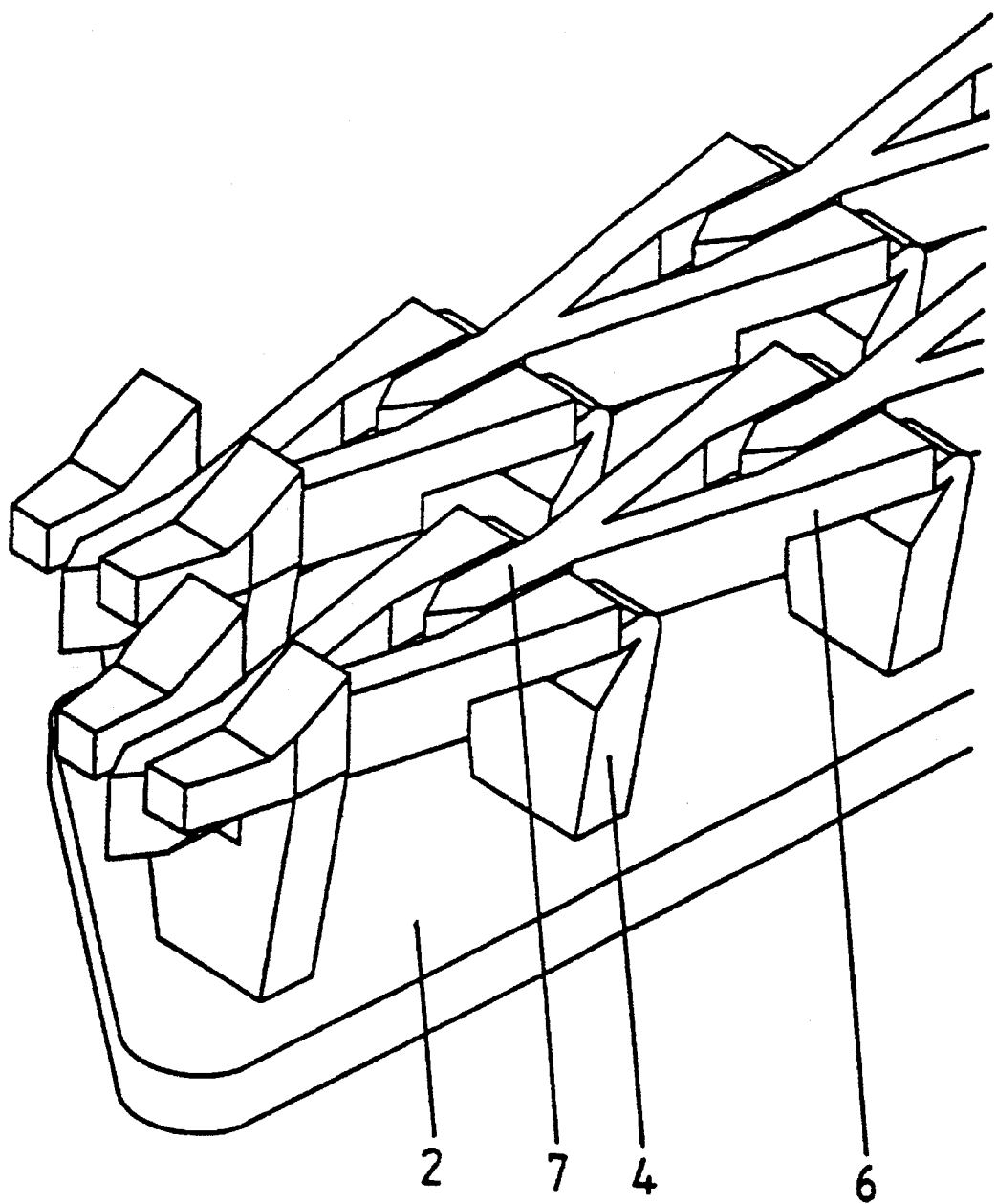
FIG. 5 is an enlarged section from FIG. 2.

The staple means 1 according to the first version shown in FIG. 1 is in the form of a comb-shaped staple strip. A plurality of staple elements 3 are firmly connected to the strip-shaped base 2. The complete staple means 1 preferably consists of a single part.

The staple elements 3 are arranged at a defined distance one behind the other in a row on the base 2, extending perpendicularly relative to the plane of the base 2.

The individual staple element 3 has a stem 4 which is designed rigid relative to the base 2. The height of the stem 4 corresponds to the thickness of the tissue layers to be clipped in the compressed state. Joined to the stem 4 is a piercer 5. The piercer 5 has a Y-shaped design according to the selected version. Via the symmetrical limbs 6 is provided a connection to the stem 4 which runs transversely relative to the base 2 and comprises a significantly smaller cross-section. The free limb 7 is designed as a tip 8 in order to penetrate the tissue layers.

Figure 6:
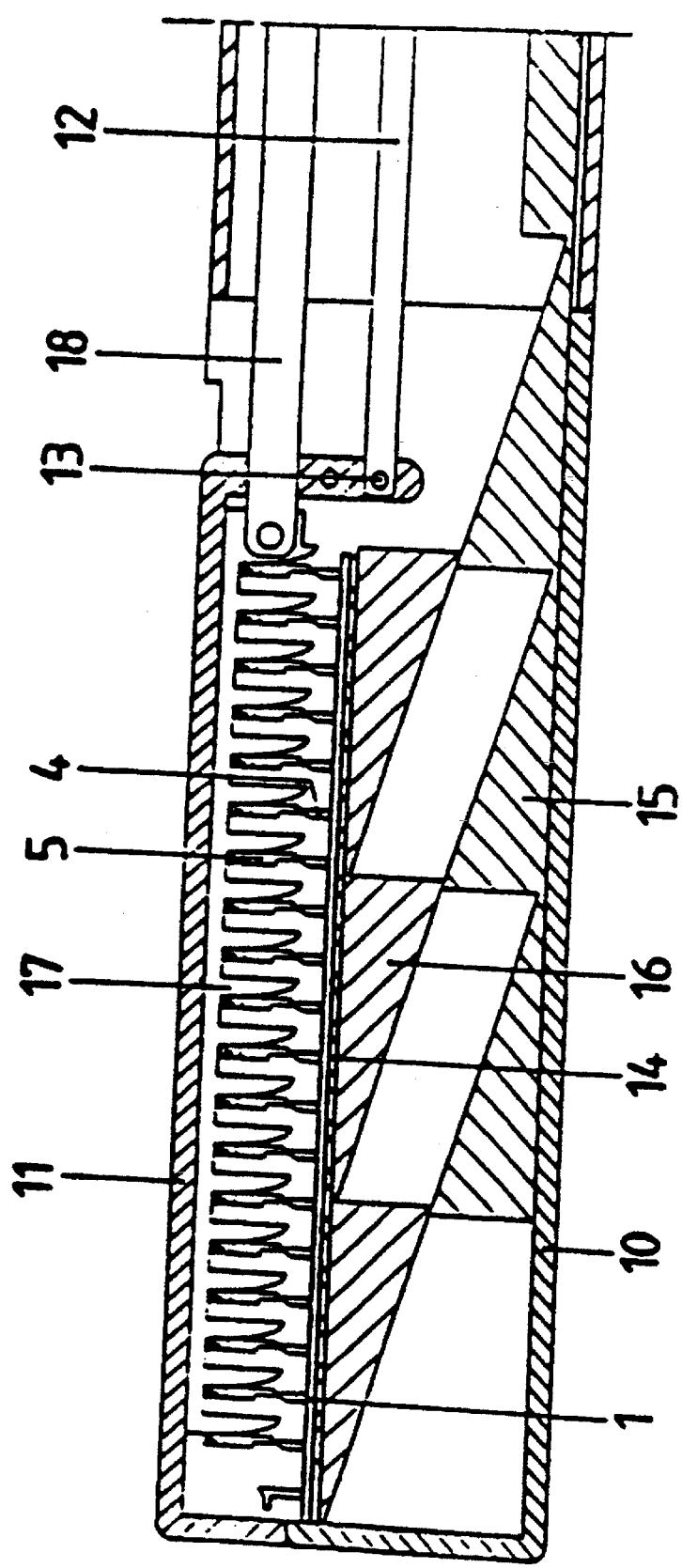
FIG. 6 is a longitudinal section through an apparatus for using the staple means according to FIG. 1.
Figure 7C:
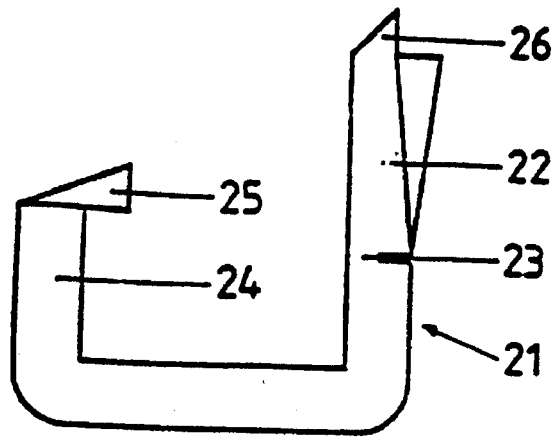
FIGS. 7a, 7b, 7c and 7d are views of a second version of a staple means.
Figure 7D:
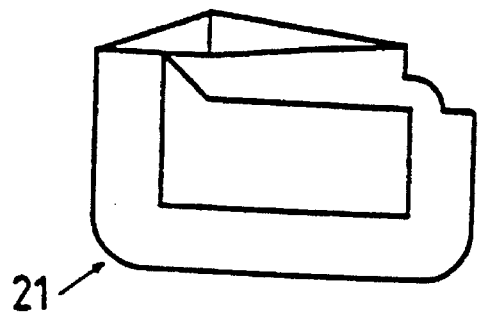
Figure 7A:
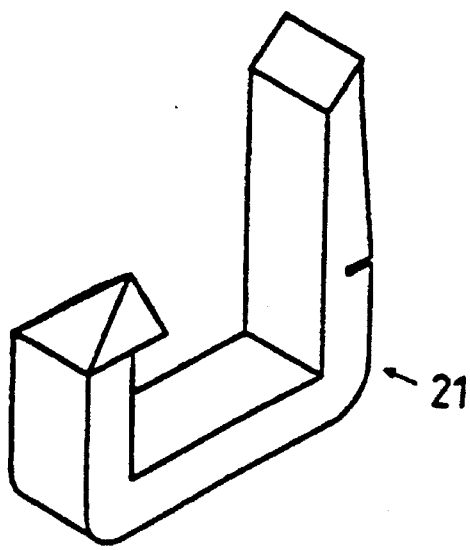
Figure 7B:
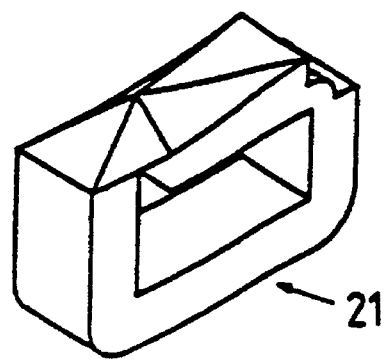

The placement of the staple means 1 takes place by means of the device shown in FIG. 6, the representation being limited to the distal end of the device. The stapling of the tissue layers takes place in this zone of the distal end of the device. To this end, this zone is essentially divided into two clamping jaws 10, 11. While the lower clamping jaw 10 is rigid relative to the part of the device (not shown), the upper clamping jaw 11 can be opened round a joint 13 by means of a push rod 12 in the manner of forceps. The lower clamping jaw 10 is provided with a support surface 14 which is displaceable transversely relative to the tissue layer, the transverse displacement being realized over a sloping plane.

The staple means 1 is fixed with its base 2 on the support surface 14. The staple elements 3 are directed with their tips 8 towards the upper clamping jaw 11. The device is made ready for reception by opening the upper clamping jaw 11. The tissue layers to be clipped are positioned between the clamping jaws 10, 11 on the lower clamping jaw 10 in such a way that the tissue layers lie on the tips 8 of the staple elements 3. After the closure of the device by swivelling of the upper clamping jaw 11 towards the lower clamping jaw 10 by means of the push rod 12 via the joint 13, the support surface 14 with the staple means 1 lying on it is pressed against the tissue layers by displacement of the wedges 15 in proximal direction with respect to the sloping plane 16 connected to the support surface 14. The piercers 5 penetrate the tissue layers, which are forced against the base 2 by a comb-shaped anvil 17 arranged in the upper clamping jaw 11 and acting between the staple elements 3.

The interaction between the transverse displacement of the support surface 14 on the one hand and the anvil 17 on the other leads to the thickness of the tissue layers being made equal to the height of the stems 4. Through displacement of the comb-shaped anvil 17 in a distal direction by means of a push rod 18 operated from the proximal end of the device, all the piercers 5 are folded over in the same direction, the bending of the piercers 5 taking place in the smaller cross-section transitional zone of the stem 4. If displacement of the anvil 17 is continued, the limb 7 of every piercer 5 is pressed into the free space, formed in front between the limbs 6 of the piercer 5. Barbs 19 are provided at the limb 7. Stop surfaces 20 provided in the limbs 6, engage barbs 19 to ensure there is a form-locking connection of neighboring piercers 5, inseparable by use according to the invention.

The stem 4 arranged at the front end of the staple means 1 does not have a piercer 5, but has corresponding locking elements for the barbs 19 of the limb 7 of a neighboring piercer 5.

The equidirectional folding over of the piercers 5 and their form-locking reciprocal retention create a top layer which guarantees a secure fixing of the tissue layers.

Opening of the clamping jaws 10, 11 releases the staple means 1, which remains as part of the wound closure in the inside of the body after the removal of the device.

The stop surfaces 20, whose length is greater than the length of the barbs 19, make possible a defined displacement, of the barbs 19 in the closed state limited in both longitudinal directions. In combination with a flexurally elastically shapable suture base 2, the closed staple means according to FIG. 1 is thus to be considered as flexurally elastic in one plane.

Depending on the type of tissue or organ and the performance of the surgical procedure, the staple means 1 can be used in one row or in several parallel rows. The staple means I is made from a resorbable material, preferably from polydioxanone.

Another version of a staple element is shown in FIGS. 7a through 7d. The U-shaped staple 21 is fitted with an elongated limb 22 which comprises a zone 23 with a significantly reduced cross-section. This zone 23 makes possible a defined bending of the elongated limb 22 in the direction of the other limb 24 of the staple 21. This limb 24 and the bent limb 22 are provided at their free ends with corresponding locking elements 25, 26 which form a closed staple 21, which cannot be opened.

In the opened state, the limbs 24 and 22 of the staple 21 are pressed through the tissue layers and closed by folding over of the elongated limb 22. In this way, the tissues to be joined are securely fixed. This staple 21 can be induced individually or in rows using a suitable device.

It is clear to the expert from the description that the design of the staple element as shown merely serves as an example. The individual staple element, in particular the section which becomes part of the suture top layer after the folding over, can be designed in many different ways without thereby leaving the scope of protection of the claims. The introduction of non-linear staples is also possible; requiring an adaptation of the staple means top layer to the suture base and therefore to a corresponding design of the corresponding locking elements of the foldable zones of the staple elements.

I claim:

1. A surgical staple comprising: a base; a top layer connected to the base via a stem, such that tissue may be pressed together between the base and the top layer; said top layer comprising a plurality of prong-shaped staple elements which are arranged perpendicular to the plane of the base; each staple element comprising a said stem, which is rigid relative to the base, and a piercer pivotally connected to the stem; the piercers being bendable for the formation of the top layer of the staple after the penetration of tissue wherein the piercers also comprise locking elements which provide locking connection of said piercers to said stems.

2. A surgical staple comprising: a base; a top layer connected to the base via a stem, such that tissue may be pressed together between the base and the top layer; said top layer comprising a plurality of prong-shaped staple elements which are arranged perpendicular to the plane of the base; each staple element comprising a said stem, which is rigid relative to the base, and a piercer pivotally connected to the stem the piercers being bendable for the formation of the top layer of the staple after the penetration of tissue characterized in that the staple is made from a resorbable material.

3. A surgical staple comprising: a base; a top layer connected to the base via a stem, such that tissue may be pressed together between the base and the top layer; said top layer comprising a plurality of prong-shaped staple elements which are arranged perpendicular to the plane of the base; each staple element comprising a said stem, which is rigid relative to the base, and a piercer pivotally connected to the stem; the piercers being bendable for the formation of the top layer of the staple after the penetration of tissue characterized in that the staple is made from polydioxanone.

* * * * *